(12) United States Patent
Nair

(10) Patent No.: US 6,737,254 B2
(45) Date of Patent: May 18, 2004

(54) SUPERCRITICAL EXTRACTION OF TAXANES

(75) Inventor: Jayaprakash B. Nair, Franklin Park, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 09/950,999

(22) Filed: Sep. 13, 2001

(65) Prior Publication Data

US 2002/0051827 A1 May 2, 2002

Related U.S. Application Data

(63) Continuation of application No. 09/404,949, filed on Sep. 24, 1999, now abandoned, which is a continuation of application No. 09/211,493, filed on Dec. 15, 1998, now abandoned, which is a continuation of application No. 07/923,011, filed on Jul. 30, 1992, now abandoned, which is a continuation of application No. 07/726,421, filed on Jul. 5, 1991, now abandoned.

(51) Int. Cl.$^7$ .............................. C12P 17/02
(52) U.S. Cl. ................. 435/110; 549/510; 424/770
(58) Field of Search ................ 435/123; 549/510; 424/770

(56) References Cited

U.S. PATENT DOCUMENTS

| | | | | |
|---|---|---|---|---|
| 4,104,409 A | * | 8/1978 | Vitzthum et al. | 426/386 |
| 4,206,221 A | * | 6/1980 | Miller et al. | 424/278 |
| 4,400,398 A | * | 8/1983 | Coenen et al. | 426/429 |
| 4,695,621 A | | 9/1987 | Allada | |
| 4,749,522 A | * | 6/1988 | Kamarei | 260/412.8 |
| 4,814,470 A | | 3/1989 | Colin et al. | |
| 4,820,517 A | * | 4/1989 | Pfeiffer et al. | 424/195.1 |
| 4,857,653 A | | 8/1989 | Colin et al. | |
| 4,876,399 A | | 10/1989 | Holton et al. | |
| 4,924,011 A | | 5/1990 | Denis et al. | |
| 4,924,012 A | | 5/1990 | Colin et al. | |
| 4,942,184 A | | 7/1990 | Haugwitz et al. | |
| 4,960,790 A | | 10/1990 | Stella et al. | |
| 4,964,995 A | * | 10/1990 | Chum et al. | 210/634 |
| 5,017,397 A | * | 5/1991 | Nguyen et al. | 426/542 |
| 5,019,504 A | * | 5/1991 | Christen et al. | 435/123 |
| 5,440,055 A | * | 8/1995 | Castor | 549/510 |
| 5,750,709 A | * | 5/1998 | Castor | 546/348 |

FOREIGN PATENT DOCUMENTS

| | | |
|---|---|---|
| DE | 2709033 | of 1978 |
| DE | 3319184 | 11/1984 |
| DE | 3704850 | 8/1988 |
| EP | 308675 | 3/1989 |
| EP | 391504 | 10/1990 |
| JP | 01226897 | 9/1989 |
| JP | 01242578 | 9/1989 |
| JP | 02157274 | 6/1990 |
| JP | 02225491 | 9/1990 |
| JP | 02292216 | 12/1990 |
| WO | WO92/07842 | 5/1992 |

OTHER PUBLICATIONS

Jennings, "High–Pressure Phase Equilibria and Supercritical Fluid Extraction Involving Carbon Dioxide System", Thesis, Georgia Institute of Technology, Jun. 1991 pp. XIII–XV, 1, 122–145.
Steinmetz E. F. Codex Vegetabilis Amsterdam #1124.*
JenningS. David W., Supercritical Extraction of Thxol. J of Supercritical Fluids, 1992 5, pp. 1–6.*
Witherup et al., *J. of Natural Products*, vol. 53, No. 5, pp. 1249–125 (Sep.–Oct. 1990).
Powell et al., *J.C.S. Chem Com.*, pp. 102–104 (1979).
Wani et al., *J. Am. Chem. Soc.*, 93, 2325–2327 (1971).
McLaughlin et al., *J. Nat. Prods.*, 44, 312–319 (1981).
Senilh et al., *J. of Nat. Prods.*, vol. 47, No. 1, pp. 131–137 (Jan.–Feb. 1984) (abstract in English).
Stasko et al., *J. of Liquid Chromotography*, 12 (11), 2133–2143 (1989).
Miller et al., *J. Org. Chem.*, 46, 1469–1474 (1981).
Kingston et al., *J. Nat. Prods.*, 45, 466–470 (1982).
Huang et al., *J. Nat. Prods.*, vol. 49, No. 4, pp. 665–669 (Jul.–Aug. 1986).
Vidensek et al., *J. Nat. Prods.*, vol. 53, No. 6, pp. 1609–1610 (Nov.–Dec. 1990).
Denis et al., *J. Am. Chem. Soc.*, 110, 5917–5919 (1988).
Magri et al., *J. Org. Chem.*, vol. 51, 3239–3242 (1986).
Smith, *Supercritical Fluid Chromatography*, RSC Chromatography Monographs, pp. 2.
Witherup et al., *Journal of Liquid Chromatography*, 12(11), 2117–2132 (1989).
Swindell et al., *J. Org. Chem.*, 55, 3–5 (1990).
Winker et al., *J. Org. Chem.*, 54, 4491–4493 (1989).
Denis et al., *J. Org. Chem.*, 51, 46–50 (1986).
Pettersson et al., *Tetrahedron Letters*, vol. 28, No. 4, 2753–2756 (1987).
Swindell et al., *Tetrahedron Letters*, vol. 28, No. 44, pp. 5275–5278 (1987).
Frejd et al., *Chemica Scripta*, 27, 561–562 (1987).
Journal, AIChe J., 34(10), pp. 1740–1742. Supercritical Extraction of *Crotalaria Spectabilis* in the Cross–Over Region; Schaeffer et al. (1988) (abstract only).
Journal, Taehan Hwahakhoe Chi, 34(6), pp. 663–672. Extraction of ginseng saponins in supercritical ammonia fluids; Oh et al. (1990) (abstract only).
Journal, ACS Symp. Ser., 406 (Supercrit. Fluid Sci. Technol.), pp. 416–433. Extraction and isolation of chemotherapeutic pyrrolizidine alkaloids from plant substrates; Schaeffer et al. (1989) (abstract only).

(List continued on next page.)

*Primary Examiner*—Irene Marx
(74) *Attorney, Agent, or Firm*—Kenneth W. Peist; Suzanne E. Babajko

(57) ABSTRACT

A method for extracting taxanes such as taxol, including the use of supercritical fluids.

20 Claims, 4 Drawing Sheets

OTHER PUBLICATIONS

Journal, Ind. Eng. Chem. Res., 28(7), pp. 1017–1020. Supercritical fluid isolation of monocrotaline from *Crotalaria spectabilis* using ion–exchange resins; Schaeffer et al. (1989) (abstract only).

Journal, J. Chromatogr. Sci., 27(2), pp. 79–85. Enrichment of tocopherols in wheat germ by directly coupled supercritical fluid extraction with semipreparative supercritical fluid chromatography; Saito et al. (1989) (abstract only).

Journal, Yukagaku, 37(9), pp. 731–735. Extraction of antimicrobial substances from dried licorice powder with supercritical carbon dioxide; Shishikura et al. (1988) (abstract only).

Journal, Pharm. Unserer Zeit, 17(4), pp. 102–105. Extraction of pharmaceuticals from the pancreas by high–pressure carbon dioxide; W. Sirtl. (1988) (abstract only).

Journal, Yakugaku Zasshi, 107(7), pp. 506–510. Application of supercritical fluid extraction to components of crude drugs and plants. III. Extraction of pigments from Lithospermum root and licorice root; Manabe et al. (1987) (abstract only).

Journal, Yakugaku Zasshi, 107(6), pp. 435–439. Application of supercritical fluid extraction to components of crude drugs and plants. II. Extraction of coumarins, lignans and prenylfavonoids; Miyachi et al. (1987) (abstract only).

Journal, Yakugaku Zasshi, 107(5), pp. 361–371. Application of supercritical fluid extraction to components of crude drugs and plants. I. Effects of pressure, temperature, time and entrainers on supercritical fluid extraction of Cnidium formosanum Yabe fruits; Miyachi et al (1987) (abstract only).

Journal, Biotechnol. Prog. 2(2), pp. 73–82. Evaluation of supercritical fluid extraction in the pharmaceutical industry; Larson et al. (1986) (abstract only).

Journal, Zhongcaoyao, 16(5), pp. 209–211, 206. Supercritical fluid extraction and its application in crude drug analysis; Zeng et al. (1985) (abstract only).

Journal, Plants Med., 50(2), pp. 171–173. Decontamination of pesticide residues in natural drugs with supercritical carbon dioxide; Stahl et al. (1984) (abstract only).

Journal, Fresenius' Z. Anal. Chem., 318(3–4), pp. 305–306. Direct coupling of high–pressure extraction using liquid and supercritical gases to high–pressure liquid chromatography; Roumeliotis et al. (1984) (abstract only).

Journal, Planta Med., 47(2), pp. 75–78. Extraction of labile natural products with supercritical gases. 12. Careful extraction of .beta.–asarone free calamus rhizomes; Stahl et al. (1983) (abstract only).

Journal, Farm. Glas., 38(10), pp. 349–358. Extraction with supercritical gases combined with thin–layer chromatography; Medic–Saric et al. (1982) (abstract only).

Journal, Mikrochim. Acta, 2(5–6), pp. 465–474. Extraction of natural substances using supercritical and liquefied gases. Part 6. Quantitative determination of the solubility of opium alkaloids; Stahl et al. (1980) (abstract only).

Journal, Planta Med., 40(3), pp. 262–270. Extraction of labile natural substances with supercritical gases. Part 4. Extraction of valepotriates from *Valeriana wallichii*; Stahl et al. (1980) (abstract only).

Journal, Arch. Pharm. (Weinheim. Ger.), 311(12), pp. 992–1001. Extraction of German chamomile with supercritical gases; Stahl et al. (1978) (abstract only).

Journal, Planta Med., 34(2), pp. 192–202. Extraction of alkaloids with supercritical gases in direct coupling with thin–layer chromatography; Stahl et al. (1978) (abstract only).

Journal, Chem.–Ing.–Tech., 48(9), pp. 773–778. Extraction with supercritical gases in direct coupling with thin–layer chromatography. Applications to natural products chemistry; Stahl et al. (1976) (abstract only).

Journal, Chem. Biochem. Eng. Q., 4(1), pp. 21–24. Supercritical extraction from solid matrixes: a preliminary study on cut tabaccos; Donsi et al. (1990) (abstract only).

Chemical Abstracts 114: 199242f; Isolation and spurification taxol drugs derived from common yew (*Taxus baccata*), Sorochinskii et al. (Inst. Biol., Kiev, USSR), *Khim.–Form. Zh*, 25(2), 45–6 (1991) (abstract only).

Chemical Abstracts 114: 94484h; Search for new anticancer substances, Guenard et al., *Recherche*, 21(226), 1427–9 (1990) (abstract only).

Chemical Abstracts 114: 164568q; Method for preparation of taxol, Holton et al., Eur. Pat. Appl. EP 400,971 (1990) (abstract only).

Chemical Abstracts 112: 158670j; Process for the preparation of taxol, Denis et al., Eur. Pat. Appl. EP 366,840 (Oct. 11, 1989) (abstract only).

Chemical Abstracts 100(11)85466n; Synthetic studies on antitumor agents: the total synthesis of quadrone; an approach to taxol, Bhagwat (1983) (abstract only).

Chemical Abstracts 114(3)24247j; Studies directed towards total synthesis of taxol. (I). An approach to the C–ring of taxol. (II). Studies on the synthesis of the A–ring of taxol, Subasinghe (1990) (abstract only).

Chemical Abstracts 107(23)217874a; I. An asymmetric synthesis of the Prelog–Djerassi lactone methyl ester. II. Studies directed toward the synthesis of taxol, Guinn (1986) (abstract only).

Chemical Abstracts 105(7)60787h; Studies directed towards total synthesis of taxane alkaloids. I. An approach to the D–ring of taxol. II. An intramolecular photocyclo–addition approach to the taxane skeleton, Amarasekara (1985) (abstract only).

Chemical Abstracts 113(1)6635j; Synthetic studies on taxane diterpenes, Horiguchi et al. (1989) (abstract only).

Chemical Abstracts 113(1)6634h; Synthetic studies on taxane diterpenes, Nagaoka et al. (1989) (abstract only).

Chemical Abstracts 112(13)119169h; Application of the vicinal hydroxyamination reaction with asymmetric induction to the hemisynthesis of taxol and analogs; Mangatal et al. (1989) (abstract only).

Chemical Abstracts 114(19)178005r; Isolation of taxol from *Taxus baccata*; Sorochinskii et al. (1990) abstract only).

Jennings et al., "Supercritical Extraction of Taxol from the Bark of *Taxus Brevifolia*", The Journal of Supercritical Fluids, 5, pp. 1–6 (1992).

Chemical Abstracts, vol. 116, No. 26, Jun. 29, 1992, Abstract No. 262349E, Jennings et al., "Supercritical extraction of taxol from the bark of *Taxus Brevifolia*".

* cited by examiner

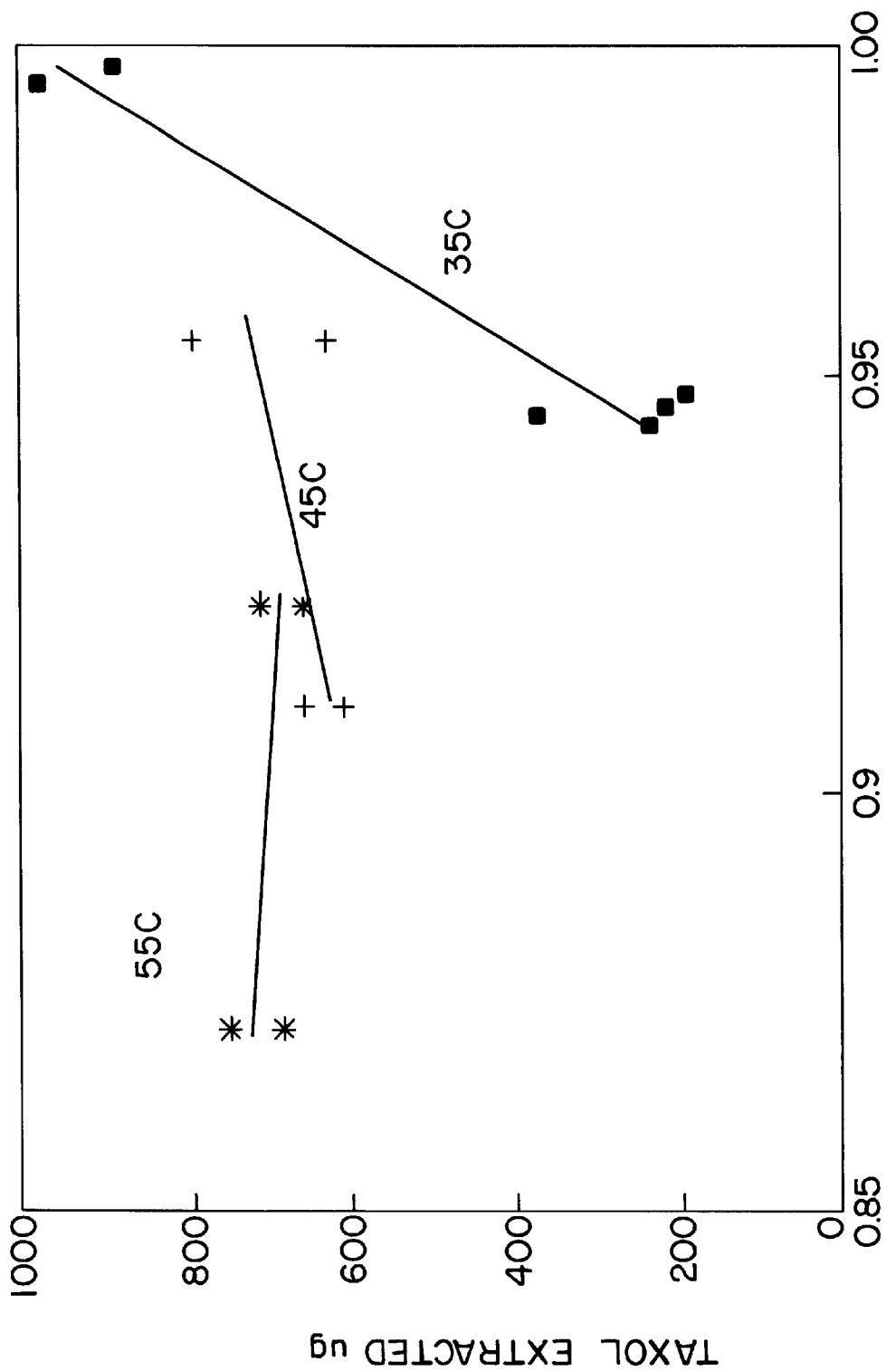

SUPERCRITICAL EXTRACTION OF TAXANES

This is a continuation of U.S. patent application Ser. No. 09/404,949, now abandoned, filed on Sep. 24, 1999, which is a continuation of U.S. patent application Ser. No. 09/211,493 filed Dec. 15, 1998, now ABN which is a continuation of U.S. patent application Ser. No. 07/923,011, filed Jul. 30, 1992, now ABN which is a continuation of U.S. patent application Ser. No. 07/726,421, filed Jul. 5, 1991, all abandoned.

FIELD OF THE INVENTION

The instant invention relates to a method for extracting taxanes from mixtures containing such compounds, and particularly for extracting taxanes from plant or plant-derived materials. The taxanes extracted may be used as pharmaceuticals, or may be used as intermediates in the preparation of pharmacologically active taxanes.

BACKGROUND OF THE INVENTION

Taxanes are diterpene compounds which find utility in the pharmaceutical field. For example, taxol, a taxane having the structure:

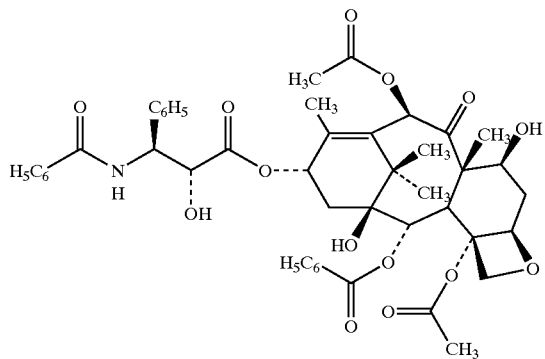

has been found to be an effective anticancer agent, particularly useful in the treatment of ovarian cancer. Cephalomannine, also a taxane, has been reported as a chemotherapeutic agent for the remission of leukemia in U.S. Pat. No. 4,206,221.

Taxanes such as those above may be found in plant materials, and have been isolated therefrom. For example, the extraction of taxol from trees of the Taxus genus using liquid methanol has been reported. However, taxanes are generally present in plant materials in relatively small amounts so that, in the case of taxol, for example, large numbers of the slow-growing yew trees forming a source for the compound may be destroyed. Further, large amounts of organic solvents may be employed in a conventional liquid extraction, which may be time consuming as well. Thus, the art has continued to search for ever more efficient and environmentally safe methods for obtaining taxanes which minimize the use of plant materials and organic solvents.

SUMMARY OF THE INVENTION

The instant invention provides a method for extracting a taxane from a mixture containing such taxane and, particularly, for extracting a taxane from a plant or plant-derived material, comprising the step of contacting the mixture with a supercritical fluid capable of solubilizing at least part of the taxane contained therein.

The instant invention provides an efficient method for obtaining taxanes from mixtures with other compounds or materials, and is especially useful in separating taxol, a potent anticancer agent, from trees of the Taxus genus.

BRIEF DESCRIPTION OF THE DRAWINGS

FIG. 4 is a graph showing the effect of density on the recovery of taxol as temperature is decreased.

DETAILED DESCRIPTION OF THE INVENTION

Figure 1:
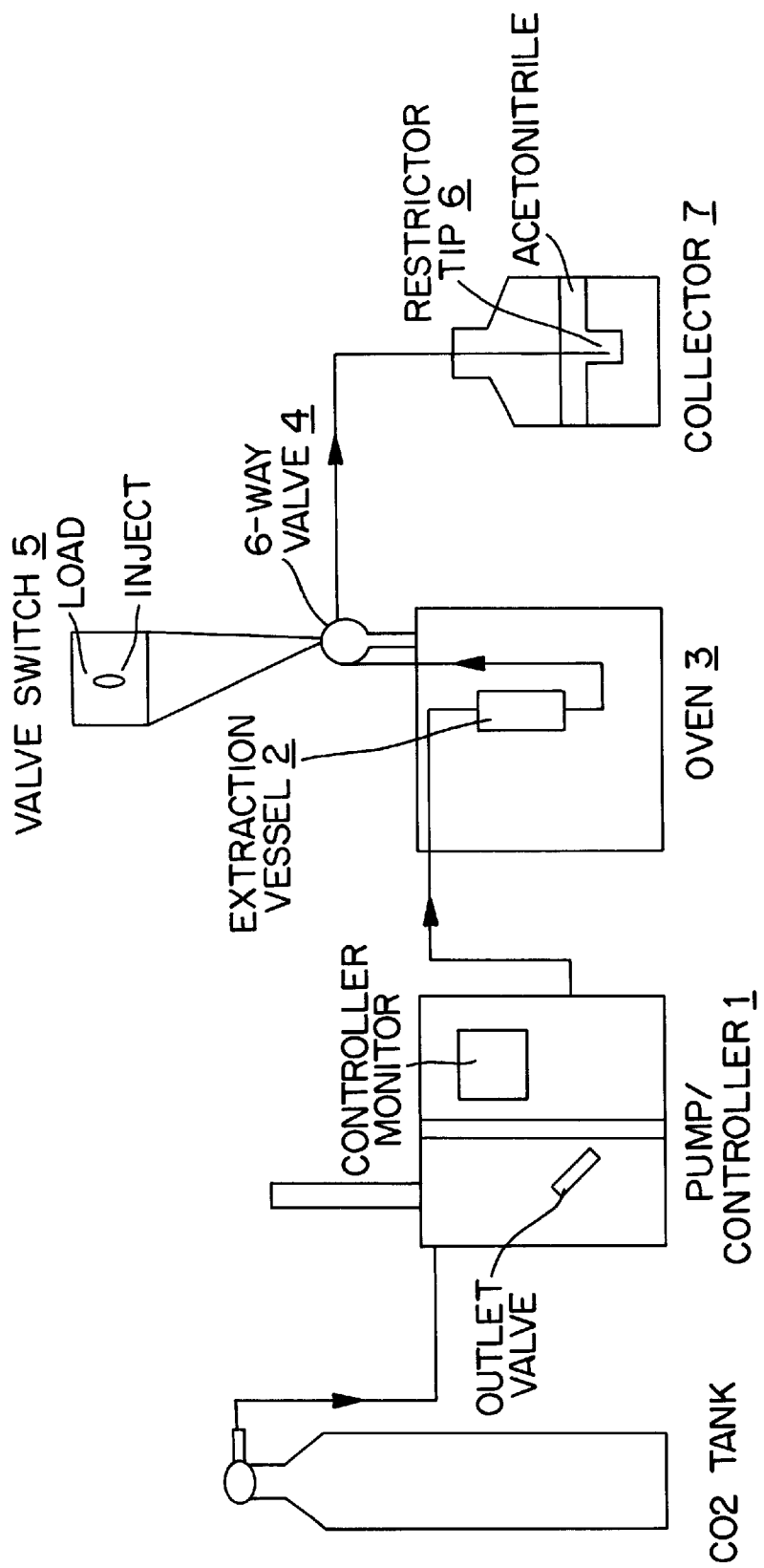
FIG. 1 is a schematic diagram of an apparatus for the method of the present invention.

Taxanes are diterpene compounds containing the taxane carbon skeleton:

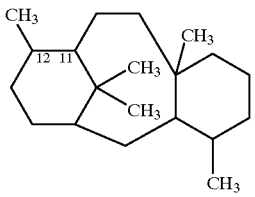

which skeleton may contain ethylenic unsaturation in the ring system thereof. The extraction of any taxane from a mixture containing such taxane is contemplated within the scope of the instant invention. It is of particular interest to separate taxanes having the above carbon skeleton wherein the 11,12-positions are bonded through an ethylenic linkage. Such taxanes include taxol, cephalomannine, baccatin III, 10-deacetylbaccatin III, and 10-deacetylcephalomannine. The term "taxane", as used in this specification, includes salts as well as solvates, of taxane compounds. Extraction of taxol is a particularly preferred embodiment of the instant invention.

The term "extraction", as used in this specification, encompasses isolation and/or purification of a taxane compound. Any mixture containing one or more taxanes in admixture with other compounds or materials may be employed in the method of the instant invention. Extraction of a single taxane, or simultaneous extraction of two or more taxanes, may be achieved according to instant method.

A preferred embodiment of the instant method relates to the separation of one or more taxanes from plant or plant-derived materials. Exemplary plant materials containing taxanes which may be employed include plants of the genera Amentotaxus, Austrotaxus, Cephalotaxus, Pseudotaxus, Taxus and Torreya. Preferred plant materials are trees of the genus Taxus such as T. brevifolia, T. baccata, T. media, T. wallichiana, T. canadensis and, especially, T. cuspidata.

Any part of the plant containing one or more taxanes may be employed such as the bark, roots, leaves or needles, branches, twigs, wood, seeds or whole seedlings. Preferably, prior to contact with the supercritical fluid, the plant material is first ground to a suitable particle size. Grinding of the plant material may be achieved by conventional means such as through use of a chipper and/or a grinding mill.

Materials derived from the aforementioned plant materials may also be employed in the method of the instant invention. The term "plant-derived material", as used in this specification, denotes any material which is obtained from a plant source and which contains one or more taxanes in admixture with other compounds. Thus, for example, an initial extraction of a plant source containing taxane may be conducted by a method such as liquid extraction, and the crude extract so obtained treated by the supercritical extraction method of the instant invention to separate a taxane therefrom.

The term "supercritical fluid" denotes fluids which are above both their critical temperature ($T_C$) and critical pressure ($P_C$), and includes both single fluids and fluid mixtures. The skilled artisan may determine whether a fluid is supercritical, that is, is at or above a temperature at which it cannot be liquified by pressure. The supercritical fluid employed in the instant invention is of a nature and quantity so as to be capable of selectively solubilizing at least part of the taxane contained in the mixture contacted. Particularly at higher pressures, use of a higher density of supercritical fluid may provide enhanced extraction. Conditions within the supercritical region are preferably selected so that decomposition of the taxane or taxanes to be extracted is minimized or completely avoided.

Exemplary supercritical fluids which may be employed include, either alone or in admixture with each other or a modifier as appropriate, nitrous oxide ($N_2O$), ammonia ($NH_3$), alkanes such as n-butane and n-pentane, sulfur hexafluoride ($SF_6$), inert gases such as Xe, haloalkanes, particulary fluoroalkanes or chlorofluoroalkanes such as $CCl_2F_2$ and $CHF_3$, and freon compounds, and, most preferably, carbon dioxide ($CO_2$) which is desirable from a safety and environmental standpoint. The term "modifier", as used in this specification, denotes any compound which, when employed in the instant method, enhances the ability of the supercritical fluid to selectively extract one or more taxanes from the mixture contacted. For example, when plant materials are employed in the instant method, the modifier may penetrate the cell wall of the plant material and facilitate contact between the supercritical fluid and taxane.

Exemplary modifiers are compounds which are solvents for the taxane to be separated, preferably good solvents in which the taxane to be separated is highly soluble. Preferred modifiers include organic solvents such as alkanols, for example, methanol, ethanol and isopropanol; aromatic hydrocarbons, for example, toluene; esters, for example, ethyl acetate; chloroalkanes, for example, chloroform ($CHCl_3$) and methylene chloride; ketones, for example, acetone; propylene carbonate; and acetonitrile. Acetone and acetonitrile are particularly preferred. Where a pharmaceutical utility for the taxane or taxanes to be extracted is contemplated, use of a pharmaceutically acceptable modifier is desirable. Acetone is preferred in the latter case.

The modifier may be contacted with the mixture, such as a plant or plant-derived material, prior to contact with the supercritical fluid and/or may be contacted with the mixture as part of the supercritical fluid. For example, in the latter case, the modifier may be pre-mixed so as to form part of the supercritical fluid.

A preferred embodiment of the instant method is that where a plant or plant-derived material is pre-contacted with the modifier, such as by pre-soaking the former with liquid modifier prior to contacting the mixture so formed with supercritical fluid. The plant or plant-derived material may be further wetted with liquid modifier, subsequent to pre-soaking and prior to contact with the supercritical fluid. Pre-soaking may be conducted for a time period as short as a few seconds, that is, providing almost instantaneous contact of the mixture with modifier and supercritical fluid, or longer if desired. Preferred times for pre-soaking are from about 1 to 5 seconds to about 1 hour.

Preferred amounts of modifier are those where the weight percent of modifier, based on the weight of fluid such as $CO_2$, is from a trace percent, for example 0.001% or less, to about 15%. It is desirable that the amount of modifier does not exceed that at which supercritical conditions may be attained at a temperature and pressure suitable from a practical standpoint.

The amount of supercritical fluid employed is a function of the type of fluid, the temperature and pressure above supercritical, the extraction equipment used, and the amount of taxane to be extracted. In general, longer contact times between supercritical fluid and the mixture containing taxane will provide enhanced recovery.

The terms "alkanell" and "alkyl", as used herein, preferably denote compounds or groups having straight or branched aliphatic hydrocarbon chains of from 1 to 12 carbons.

The term "haloalkane", as used herein, preferably denotes alkanes as described above substituted with one or more halogen atoms selected from chlorine, fluorine, bromine and iodine. The term "chloroalkane", as used herein, preferably refers to such compounds which are substituted by one or more chlorine atoms.

The term "alkanol", as used herein, preferably denotes alkanes as described above, substituted with one or more hydroxyl groups.

The terms "aromatic hydrocarbon" and "aromatic hydrocarbyl", as used herein, preferably denote compounds or groups having an aromatic ring system of from 6 to 12 carbon atoms, optionally substituted with one or more alkane groups as described above.

The term "ester", as used herein, preferably denotes compounds of the formula

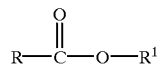

where R and $R^1$ are independently selected from alkyl and aromatic hydrocarbyl groups as described above.

The term "ketone", as used herein, preferably denotes compounds of the formula

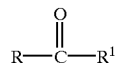

where R and $R^1$ are as described above.

The method of the instant invention may be conducted in a continuous, semi-batch or batch mode.

A particularly preferred embodiment of the instant invention is that where taxol is extracted from a mixture, preferably from a plant or plant-derived material, using a supercritical fluid and a modifier. Preferably, the supercritical fluid is carbon dioxide and the modifier is acetone or acetonitrile. It is preferred to employ carbon dioxide at pressures greater than about 72.9 atm, more preferably from about 300 to about 700 atm, particularly from about 400 to about 500 atm, and temperatures greater than about 31.3° C., more preferably from about 32° C. to 55° C., particularly from about 35° C. to about 45° C.

Subsequent to contact with the mixture, such as the plant or plant-derived material, the supercritical fluid will contain a quantity of taxane. The supercritical fluid containing taxane may then be separated from the mixture. Separation of the taxane from the supercritical fluid may be achieved by lowering the pressure and/or the temperature of the fluid to a subcritical condition at which the taxane is less soluble. The supercritical fluid containing taxane may be depressurized in one or more stages, where, when more than one stage is employed, the subsequent stage is at a lower pressure than the preceding stage. Preferably, the supercritical fluid containing taxane is depressurized into an open chamber or into a liquid solvent maintained at subcritical pressure and temperature, most preferably atmospheric pressure and room temperature. As the supercritical fluid containing taxane enters the chamber or solvent, the fluid equilibrates to or approaches the subcritical conditions at which the chamber or liquid solvent is kept, and, in the former case, the taxane is deposited, while in the latter case the taxane is taken up, by dissolution, into the liquid solvent. The subcritical conditions are preferably selected so that the fluid, originally supercritical, becomes a gas which separates off, for example, from the liquid solvent containing dissolved taxane.

Further purification of the taxane obtained may be achieved, if desired, by the use of one or more additional stages of supercritical extraction according to the instant method. Conventional methods of purification may also be employed, such as high pressure liquid chromatography, thin layer chromatography, column chromatography or liquid extraction. Supercritical fluid chromatography (SFC) may also be employed. Additional purification may be used, for example, to separate one taxane from another when two or more taxanes have been extracted from a mixture containing other compounds or materials according to the instant invention. Preferably, the taxane is ultimately obtained in substantially pure form.

As discussed above, taxanes are compounds which find utility in the pharmaceutical field, particularly as anticancer agents. Taxol is exemplary of the pharmacologically active taxanes which also include, for example, cephalomannine. The pharmacologically active taxanes may be used to treat patients suffering from cancers such as ovarian cancer, melanoma, breast, colon or lung cancer, and leukemia. Other pharmacologically active compounds which may be obtained by the method of the invention are taxanes bearing a xylose unit at C-7, such as those described in Senilh et al., *Journal of Natural Products*, Vol. 47, No. 1, pp. 131–137 (January–February 1984).

The term "patients", as used herein, preferably refers to mammals such as dogs, cats, and other domestic animals and, most preferably, refers to humans. Pharmacologically active taxanes may be administered by means selected by the skilled artisan such as oral or parenteral means, and in effective dosages which may also be selected according to methods known to the skilled artisan. Effective dosages are those which allow mitigation or cure of the malady for which treatment is sought, such as dosages which maintain or decrease the size of a tumor. Generally, an effective dose is in the range of about 0.5 to about 5.0 mg/kg of body weight per day. The pharmacologically active taxane may be employed alone, or in conjunction with other compounds effective for treatment and/or inert substances such as pharmaceutically acceptable diluents or carriers.

Taxanes obtained by the method of the instant invention may also be used as intermediates to prepare other, pharmacologically active taxanes, the latter which may be used as described above. The method of the instant invention may thus facilitate preparation of such pharmacologically active taxanes by providing an efficient means for obtaining the taxane starting material.

Exemplary taxanes which may be obtained by the method of the instant invention and which may be used as intermediates in the preparation of pharmacologically active taxanes include cephalomannine, baccatin III, 10-deacetylbaccatin III, and 10-deacetylcephalomannine. Methods known to the skilled artisan may be employed to convert the taxane intermediate to the pharmacologically active taxane desired. For example, Denis et al., *J. Am. Chem. Soc.*, 110, 5917–5919 (1988) describes a method for converting 10-deacetylbaccatin III to taxol. Reductive cleavage of the C-13 side chain, for example, allowing the conversion of cephalomannine to taxol, is described by Magri et al., *J. Org. Chem.*, Vol. 51, No. 16, 3239–3242 (1986). The taxane to be converted may be inactive, although conversion of one active taxane to another taxane, the latter of which is effective for treatment of a different malady, or possesses greater potency than the starting material, is contemplated.

The following examples are provided to illustrate the method of the invention, and are not intended to limit the scope of the instant claims.

EXAMPLE

Supercritical Extraction of Taxol from *Taxus cuspidata*

A. Extraction Apparatus

FIG. 1 illustrates the arrangement of the components used for the following extractions. Liquid carbon dioxide was pressurized by the pump/controller (1) (Suprex SFE-50 Microextractor with a syringe pump from Suprex Corp.). Opening the outlet valve on the pump sent the supercritical carbon dioxide to the extraction vessel (2) (stainless steel HPLC guard column (21.2 mm×100 mm) rated to 6000 psi with stainless steel frits and access to either end of the column). The extraction vessel was maintained at a constant temperature in an oven (3). In the oven, the liquid carbon dioxide was above its critical temperature and critical pressure, and thus was maintained in the supercritical state. A six-way valve (4) controlled and directed the supercritical carbon dioxide from the extraction vessel. When the valve switch (5) was in the inject mode, the supercritical fluid filled the extraction vessel for a static extraction. When the valve was switched to the load mode, the supercritical fluid was released to the restrictor (a 30-cm length of 0.020 inch i.d. stainless steel tubing, crimped on the very tip to restrict carbon dioxide flow) for a dynamic extraction. The restrictor tip (6) was immersed in the fluid contained in the collector (7) (a 1-liter HPLC solvent reservoir).

The restrictor was employed to maintain high pressures within the extraction vessel while venting the supercritical fluid out of the system. Extraction of plant material may plug the small inner diameter of commercially available restrictors. To produce a reproducible restrictor for maintenance of high back pressures, with a minimum of plugging, a modification was made to the commercially available restrictor design.

A 20 mm length of 5 $\mu$m stainless steel tubing was smoothly cut with a tubing cutter. The tubing was fitted with a stainless steel ferrule which was tightened to the tubing with a female adaptor. A male union was placed on the restrictor and the end opposite of the ferrule crushed with a large table vise that evenly crimped the very end of the tip (2 mm).

The tip of the restrictor was adjusted as follows. To the end of a length of 20 $\mu$m stainless steel tubing, the male fitting was attached and joined with a double female union that was drilled out to 20 μm internal diameter. The restrictor was attached to the union and the tip was connected to a digital bubble flow meter. The flow was monitored through the restrictor at an operating pressure of 430 atm. The wide part of the crimp was opened as needed with a pair of pliers to maintain a flow rate fast enough to flush out the compounds of interest, but slow enough that there was no aerosol formation that could lead to compound loss. A restrictor flow of 400 ml/min was employed to accomplish this.

B. Extraction Procedure

Milled plant material (*Taxus cuspidata*, 10±0.1 g) was weighed out into a plastic weighing boat. With a graduated cylinder, 10 ml acetonitrile was measured out and distributed over the plant material, and mixed well with a spatula. The weighing boat was covered to avoid evaporation of the acetonitrile. The sample was allowed to soak for 20 minutes.

A small piece of silanized glass wool was placed into, and was pushed to the bottom of, the extraction vessel. Enough glass wool was used to obtain a depth of approximately 1 cm.

With a powder funnel, the extraction vessel was filled with the soaked material, and packed with a glass rod. When all of the material had been transferred into the extraction vessel, an additional 5 ml of acetonitrile were added to the sample in the vessel. The material filled the extraction vessel such that there was about 2 cm of free space above the sample. This void was filled with another plug of glass wool (approximately 2 cm thick).

Static Extraction

The pump was brought to operating pressure, and the outlet valve opened to fill the extraction vessel with supercritical carbon dioxide. Conditions at this point were such that liquid carbon dioxide was present in the extraction vessel. The system was allowed to equilibrate to the supercritical operating pressure and temperature set forth in Table I. Once the set temperature and pressure were attained, timing of the static extraction was begun. The density report displayed by the controller monitor was observed.

Dynamic Extraction

After 30 minutes of static extraction, the valve was switched to deliver the supercritical fluid to the collector. The collector contained 50 ml of acetonitrile into which the restrictor tip was submerged about 1.5–2.0 inches. The timer was set for another 30 minutes, during which bubbling at the tip of the restrictor was observed. After 30 minutes, the valve was again switched, and the restrictor allowed to depressurize. The acetonitrile in the collector was deep green in color at this time.

Sample Collection

The contents of the collector were transferred into two 50 ml tubes. The collector was washed with 5 ml acetonitrile which was combined with the contents of the tubes. The sample volume was reduced to dryness by rotary evaporation, and the amount of the residue was weighed. The residue was reconstituted in 1.0 ml acetonitrile. This extracted taxol solution was maintained at −20° C. until analysis by HPLC.

C. Results

Duplicate extractions were made under each set of the conditions listed in Table I to check the extraction reproducibility. Table II shows the amounts of taxol extracted, under the various conditions of temperature and pressure.

Figure 2:
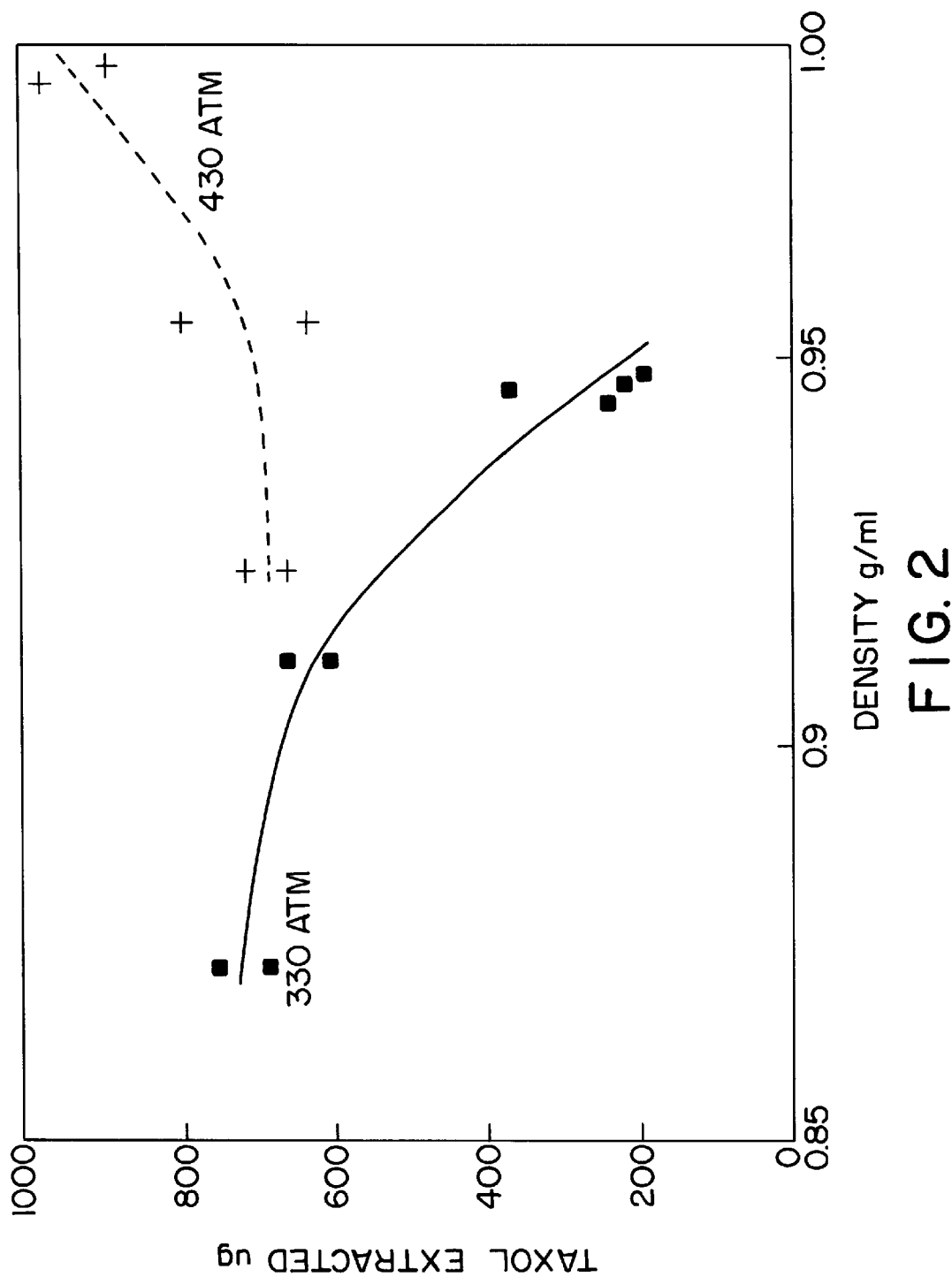
FIG. 2 is a graph demonstrating the relation of the amount of taxol extracted to the density at two pressures.
Figure 3:
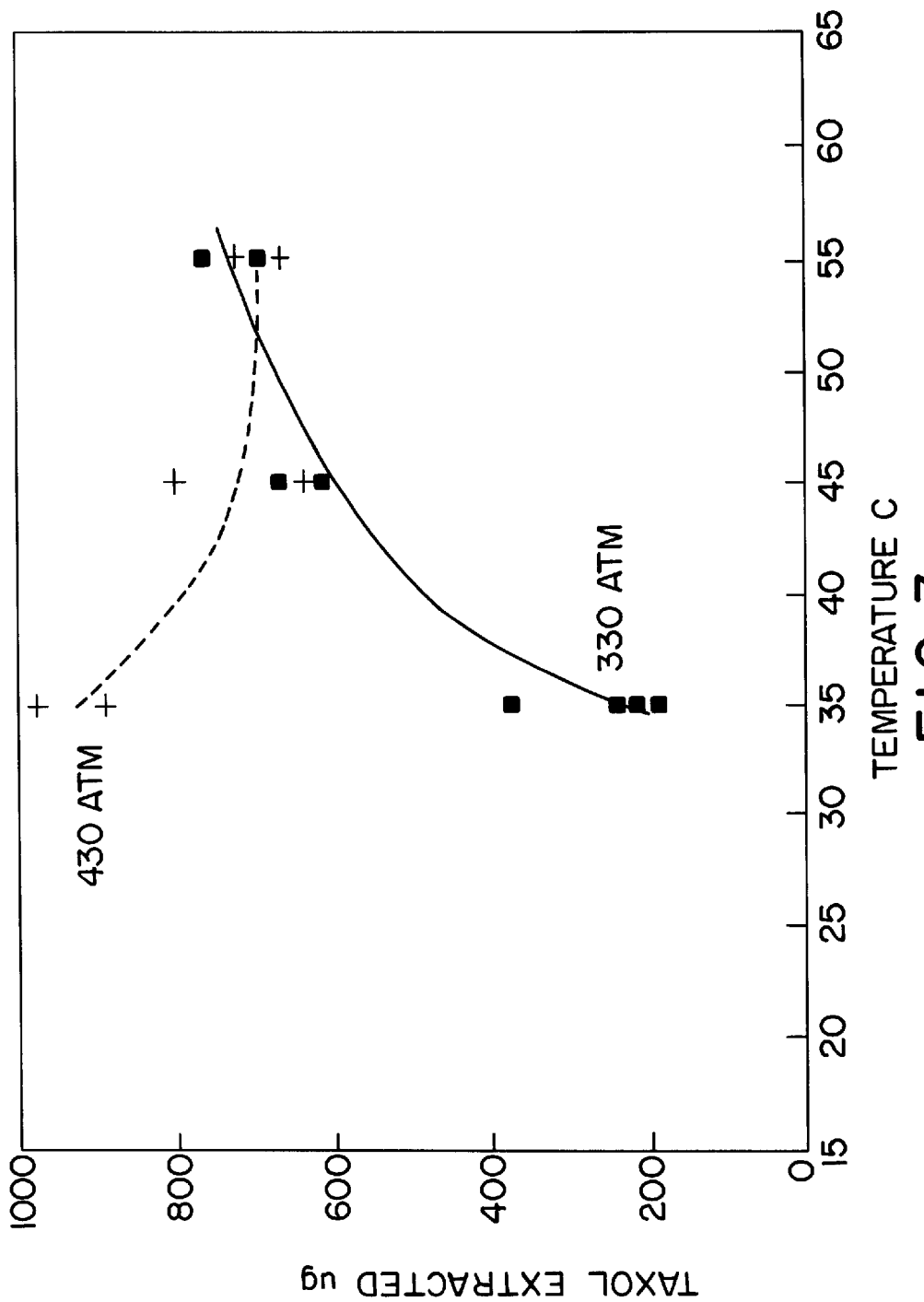
FIG. 3 is a graph showing the relation of the amount of taxol extracted to temperature.

FIG. 2 illustrates the relation of the amount of taxol extracted to the density at two pressures. Extraction at a high pressure and a low temperature provides the highest density and, at 430 atm, the highest taxol recovery. A temperature of 35° C. and a pressure of 430 atm were the best conditions for this extraction within the temperature and pressure ranges examined. FIG. 3 illustrates the relation of the amount of taxol extracted to the temperature. FIG. 4 shows the increased influence of density on the recovery of taxol as the set temperature is decreased.

Extractions of milled plant material without acetonitrile wetting gave no detectable amounts of taxol. Modification of supercritical carbon dioxide was thus employed.

TABLE I

EXTRACTION CONDITIONS

| Temperature (° C.) | Pressure (atm) |
|---|---|
| 35 | 330 |
| 45 | 330 |
| 55 | 330 |
| 35 | 430 |
| 45 | 430 |
| 55 | 430 |

TABLE II

| Sample | μg Taxol Extracted* | Temperature (° C.) | Pressure (atm) | Density (g/mL) |
|---|---|---|---|---|
| RA-I | 238 | 35 | 330 | 0.945 |
| RA-II | 197 | 35 | 330 | 0.948 |
| RA-III | 222 | 35 | 330 | 0.947 |
| RA-IV | 367 | 35 | 330 | 0.946 |
| RB-I | 603 | 45 | 330 | 0.911 |
| RB-II | 654 | 45 | 330 | 0.911 |
| RC-I | 684 | 55 | 330 | 0.872 |
| RC-II | 751 | 55 | 330 | 0.872 |
| RD-I | 969 | 35 | 430 | 0.985 |
| RD-II | 883 | 35 | 430 | 0.987 |
| RE-I | 790 | 45 | 430 | 0.955 |
| RE-II | 625 | 45 | 430 | 0.955 |
| RE-III | 555 | 45 | 430 | 0.955 |
| RF-I | 655 | 55 | 430 | 0.923 |
| RF-II | 710 | 55 | 430 | 0.923 |
| RF-III | 510 | 55 | 430 | 0.923 |

*Per 10.0 g plant material

EXAMPLE 2

Supercritical Extraction of Taxol from *Taxus cuspidata*: Use of Higher Pressure The extraction procedure of Example 1 was followed, with the exception that a pressure of 680 atm, and a temperature as indicated in Table III, was employed, and the apparatus used was a Model 703 Dionex supercritical extractor. Taxol was extracted in amounts also shown in Table III.

TABLE III

| Sample | μg Taxol extracted per 10 g plant material | Temp (° C.) | Density (g/ml) |
|---|---|---|---|
| DX1 | 320 | 35 | 1.086 |
| DX2 | 500 | 35 | 1.086 |
| DX3 | 380 | 35 | 1.086 |
| DX4 | 580 | 35 | 1.086 |
| DX5 | 680 | 45 | 1.065 |

EXAMPLE 3

Supercritical Extraction of Taxol from *Taxus cuspidata*: Methanol as Modifier

The extraction procedure of Example 1 was followed, with the exception that methanol was employed in place of acetonitrile as the modifier. The temperature and pressure employed, and the amount of taxol extracted, is shown in Table IV.

TABLE IV

| Sample | μg Taxol extracted per 10 g plant material | Temp (° C.) | Pressure (atm) | Density (g/ml) |
|---|---|---|---|---|
| RG-II | 350 | 45 | 330 | 0.911 |
| RG-III | 60 | 45 | 330 | 0.908 |
| RH-I | 30 | 35 | 430 | 0.987 |
| RH-II | 240 | 35 | 430 | 0.987 |
| RH-III | 162 | 35 | 430 | 0.987 |
| RJ-IA | 240 | 35 | 430 | 0.987 |
| RK-I | 420 | 45 | 430 | 0.954 |
| RK-II | 210 | 45 | 430 | 0.954 |
| RL-I | 420 | 55 | 430 | 0.923 |

What is claimed is:

1. The method for extracting a taxane from a mixture containing said taxane, comprising the step of contacting the mixture with a supercritical fluid in admixture with a solvent modifier selected from the group consisting of acetonitrile, methanol and acetone, under conditions and for a time sufficient to solubilize the taxane in said mixture, and separating said taxane from the supercritical fluid and modifier to obtain a substantially pure taxane product, capable of solubilizing at least part of the taxane contained therein, said contacting a conditions suitable for selectively solubilizing said taxane and for minimizing or avoiding the decomposition of the taxane thus extracted.

2. The method of claim 1, wherein at least one of the group consisting of taxol, cephalomannine, baccatin III, and 10-decactylcephalomannine are extracted.

3. The method of claim 2, wherein taxol is extracted.

4. The method of claim 1, wherein said mixture is a plant or plant-derived material.

5. the method of claim 4, wherein said plant material is selected from one or more of the genus Amentotaxus, Austrotaxus, Cephalotaxus, Pseudotaxus, Taxus, and Torreya.

6. The method of claim 5, wherein said plant material is from a tree of the Taxus genus.

7. The method at claim 6, wherein said tree is selected tram the group consisting of: *T. brevifolia, T. baccata, T. media, T. wallichiana, T. canadensis* and *T. cuspidata*.

8. The method of claim 5, wherein said plant material includes one or more parts of the plant selected from bark, roots, leaves, needles, branches, twigs, wood, seeds and whole seedlings.

9. The method of claim 1, wherein said supercritical fluid includes at least one of the group consisting of: nitrous oxide, ammonia, an alkane, sulfur hexafluoride, an inert gas, a haloalkane, and carbon dioxide.

10. The method of claim 9, wherein said supercritical fluid is carbon dioxide.

11. The method of claim 1, wherein said modifier is acetonitrile.

12. The method of claim 10 further comprising the step of pre-contacting a plant or plant-derived material in liquid form with the modifier prior to contacting the mixture with supercritical carbon dioxide.

13. The method of claim 10, wherein the pressure of the carbon dioxide employed is greater than about 72.9 atm.

14. The method of claim 13, wherein the pressure of the carbon dioxide employed is from about 400 to about 500 atm.

15. The method of claim 10, wherein the temperature of the carbon dioxide employed is greater than about 31.3° C.

16. The method of claim 15, wherein the temperature of the carbon dioxide employed is from about 35° C. to about 45° C.

17. The method of claim 1, wherein said separating step includes depressurizing said supercritical fluid containing said taxane into an open chamber or into a liquid solvent for said taxane.

18. A method for extracting a chemotherapeutic taxane from a mixture including a plant material or a plant derived material containing said taxane, comprising the steps of:

a. pre-contacting said material with a modifier that is a solvent for said taxane;

b. contacting said material with a supercritical fluid under conditions and for a time which allows selective solubilization of said taxane in said supercritical fluid; and c. separating said taxane from said supercritical fluid to obtain a substantially pure taxane product.

19. The method of claim 18, wherein said supercritical fluid is carbon dioxide and said modifier is acetonitrile or methanol.

20. The method of claim 19, wherein said supercritical fluid is contacted with said material at a temperature of about 35° C. and a pressure of about 430 atm.

* * * * *